US00PP21308P2

(12) United States Plant Patent
Niederländer

(10) Patent No.: US PP21,308 P2
(45) Date of Patent: Sep. 21, 2010

(54) ***ASTER* PLANT NAMED 'KIASTGRANA'**

(50) Latin Name: ***Aster novi-belgii*×*Aster dumosus***
Varietal Denomination: Kiastgrana

(75) Inventor: Andreas Niederländer, Gensingen (DE)

(73) Assignee: Kientzler GmbH & Co. KG, Gensingen (DE)

( * ) Notice: Subject to any disclaimer, the term of this patent is extended or adjusted under 35 U.S.C. 154(b) by 0 days.

(21) Appl. No.: 12/387,563

(22) Filed: May 4, 2009

(51) Int. Cl.
*A01H 5/00* (2006.01)

(52) U.S. Cl. ..... Plt./355

(58) Field of Classification Search ..... Plt./355
See application file for complete search history.

(56) References Cited

OTHER PUBLICATIONS

GTITM UPOVROM Citation for 'Kiastgrana' as per QZ PBR 20082525; Nov. 10, 2008.*

* cited by examiner

*Primary Examiner*—Kent L Bell
(74) *Attorney, Agent, or Firm*—C. A. Whealy

(57) ABSTRACT

A new and distinct cultivar of *Aster* plant named 'Kiastgrana', characterized by its compact, upright, uniform and mounded plant habit; freely branching growth habit; semi-double type inflorescences with red purple-colored ray florets; and tolerance to Powdery Mildew.

1 Drawing Sheet

Botanical designation: *Aster novi-belgii*×*Aster dumosus*.
Cultivar denomination: 'Kiastgrana'.

BACKGROUND OF THE INVENTION

The present invention relates to a new and distinct cultivar of *Aster* plant, botanically known as *Aster novi-belgii*×*Aster dumosus* and hereinafter referred to by the name 'Kiastgrana'.

The objective of the breeding program is to create new compact *Aster* cultivars with uniform growth habit, freely branching habit and attractive ray floret color.

The new *Aster* plant originated from a cross-pollination in September, 2004, in Gensingen, Germany of *Aster novi-belgii* 'Jenny', not patented, as the female, or seed, parent *Aster dumosus* 'Kassel', not patented, as the male, or pollen, parent. The new *Aster* was discovered and selected by the Inventor as a single flowering plant within the progeny of the stated cross-pollination in a controlled greenhouse environment in Gensingen, Germany in September, 2005.

Asexual reproduction of the new *Aster* plant by vegetative tip cuttings was first conducted in a controlled greenhouse environment in Gensingen, Germany in June, 2007. Asexual reproduction by vegetative tip cuttings has shown that the unique features of this new *Aster* plant are stable and reproduced true to type in successive generations.

SUMMARY OF THE INVENTION

Plants of the new *Aster* have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Kiastgrana'.

These characteristics in combination distinguish 'Kiastgrana' as a new and distinct potted *Aster* cultivar:

1. Compact, upright, uniform and mounded plant habit.
2. Freely branching growth habit.
3. Semi-double type inflorescences with red purple-colored ray florets.
4. Tolerance to Powdery Mildew.

Plants of the new *Aster* differ from plants of the female parent, 'Jenny', in the following characteristics:

1. Inflorescences of plants of the new *Aster* have more ray florets than inflorescences of 'Jenny'.
2. Ray floret color of plants of the new *Aster* resists fading whereas ray floret color of plants of 'Jenny' fades.

Plants of the new *Aster* differ from plants of the male parent, 'Kassel', in the following characteristics:

1. Plants of the new *Aster* are larger than plants of 'Kassel'.
2. Inflorescences of plants of the new *Aster* have more ray florets than inflorescences of 'Kassel'.
3. Plants of the new *Aster* and 'Kassel' differ in ray floret color as plants of 'Kassel' have pink-colored ray florets.

Plants of the new *Aster* can be compared to plants of 'Pink Topas', not patented. In side-by-side comparisons conducted in Gensingen, Germany, plants of the new Aster differed from plants of 'Pink Topas' in the following characteristics:

1. Plants of the new *Aster* were more compact than plants of 'Pink Topas'.
2. Plants of the new *Aster* flowered earlier than plants of 'Pink Topas'.
3. Inflorescences of plants of the new *Aster* had more ray florets than plants of 'Pink Topas'.
4. Plants of the new *Aster* and 'Pink Topas' differed in ray floret color as plants of 'Pink Topas' had lighter-colored ray florets.

Plants of the new Aster can be compared to plants of 'Purple Diamond', not patented. In side-by-side comparisons conducted in Gensingen, Germany, plants of the new Aster differed from plants of 'Purple Diamond' in the following characteristics:

1. Plants of the new *Aster* were more vigorous than plants of 'Purple Diamond'.
2. Plants of the new *Aster* flowered earlier than plants of 'Purple Diamond'.
3. Inflorescences of plants of the new *Aster* had more ray florets than plants of 'Purple Diamond'.
4. Plants of the new *Aster* and 'Purple Diamond' differed in ray floret color as plants of 'Purple Diamond' had lighter-colored ray florets.

BRIEF DESCRIPTION OF THE PHOTOGRAPHS

The accompanying photographs illustrate the overall appearance of the new Aster. These photographs show the colors as true as it is reasonably possible to obtain in colored reproductions of this type. Colors in the photographs may differ slightly from the color values cited in the detailed botanical description which accurately describe the colors of the new *Aster*.

The photograph at the bottom of the sheet comprises a side perspective view of a typical flowering plant of 'Kiastgrana' grown in a container.

The photograph at the top of the sheet is a close-up view of a typical inflorescence and a typical inflorescence bud of 'Kiastgrana'.

DETAILED BOTANICAL DESCRIPTION

The aforementioned photographs and following observations and measurements describe plants grown during the spring in Carleton, Mich. in a polycarbonate-covered greenhouse and under conditions and practices which approximate those generally used in commercial *Aster* production. During the production of the plants, day temperatures ranged from 20° C. to 24° C. and night temperatures ranged from 18° C. to 22° C. Plants were grown in 20-cm containers and were pinched three times. Plants were 29 weeks old from planting when the description and photographs were taken. In the following description, color references are made to The Royal Horticultural Society Colour Chart, Fifth Edition, 2007, except where general terms of ordinary dictionary significance are used.

Botanical classification: *Aster novi-belgii*×*Aster dumosus* 'Kiastgrana'.

Parentage:

*Female, or seed, parent.*—*Aster novi-belgii* 'Jenny', not patented.

*Male, or pollen, parent.*—*Aster dumosus* 'Kassel', not patented.

Propagation:

*Type.*—Terminal vegetative cuttings.

*Time to initiate roots, summer.*—About six to eight days at temperatures of 18° C. to 20° C.

*Time to initiate roots, winter.*—About eight to twelve days at temperatures of 18° C. to 20° C.

*Time to produce a rooted young plant, summer.*—About 18 days at average temperatures of 18° C. to 20° C.

*Time to produce a rooted young plant, winter.*—About 22 days at average temperatures of 18° C. to 20° C.

*Root description.*—Fine, fibrous; white in color. Rooting habit: Moderately freely branching; moderately dense.

Plant description:

*Appearance.*—Herbaceous semi-double type Aster; compact, upright growth habit; inverted triangle with uniformly mounded crown; Freely branching growth habit with about 56 lateral branches developing per plant; dense and full plants; vigorous growth habit.

*Plant height.*—About 12 cm.

*Plant width.*—About 23 cm.

*Lateral branches.*—Length: About 10 cm. Diameter: About 1 mm. Internode length: About 0.25 cm to 1.4 cm. Strength: Strong. Texture: Smooth, glabrous. Color: Close to 146B.

Foliage description:

*Arrangement.*—Alternate, simple.

*Length.*—About 9 cm.

*Width.*—About 2 cm.

*Shape.*—Oblanceolate.

*Apex.*—Acute.

*Base.*—Attenuate; decurrent.

*Margin.*—Entire to sparsely serrate.

*Texture, upper and lower surfaces.*—Smooth, glabrous.

*Venation pattern.*—Pinnate, arcuate.

*Color.*—Developing leaves, upper surface: Close to 139B. Developing leaves, upper surface: Close to 138A. Fully expanded leaves, upper surface: Close to N137A; venation, close to 137B. Fully expanded leaves, lower surface: Close to 146A; venation, close to 146B.

*Petioles.*—Length: About 5.3 cm. Width: About 3 mm. Texture, upper and lower surfaces: Smooth, glabrous. Color, upper surface: Close to 145C. Color, lower surface: Close to 145B.

Inflorescence description:

*Appearance.*—Semi-double type inflorescence form with lanceolate-shaped ray florets; inflorescences borne on terminals above and beyond the foliar plane; ray and disc florets arranged acropetally on a capitulum.

*Fragrance.*—None detected.

*Flowering response.*—Under natural conditions, plants flower in the late summer through the autumn in the Northern Hemisphere.

*Inflorescence longevity.*—Inflorescences last about one week on the plant; inflorescences persistent.

*Inflorescence bud.*—Height: About 8 mm. Diameter: About 6 mm. Shape: Ovoid. Color: Close to 70B to 70C.

*Inflorescence size.*—Diameter: About 3.3 cm. Depth (height): About 1.5 cm. Diameter of disc: About 8 mm Receptacle height: About 9 mm. Receptacle diameter: About 1.1 cm. Receptacle color: Close to 137B.

*Ray florets.*—Length: About 1.7 cm. Width: About 3 mm. Shape: Lanceolate. Apex: Shallowly emarginate. Base: Acute. Margin: Entire. Texture, upper and lower surfaces: Smooth, glabrous; satiny. Orientation: Initially upright, then close to perpendicular to peduncle. Number of ray florets per inflorescence: About 62 arranged in about three to four whorls. Color: When opening, upper surface: Close to 72A. When opening, lower surface: Close to 76A. Fully opened, upper surface: Close to 70A; color resists fading. Fully opened, lower surface: Close to 76A to 76B; color resists fading.

*Disc florets.*—Arrangement: Massed at center of receptacle. Shape: Tubular, elongated. Apex: Five-pointed.

Length: About 7 mm. Width: About 2 mm. Number of disc florets per inflorescence: About 38. Texture: Smooth, glabrous. Color, immature: Apex: Close to 153C. Mid-section: Close to 154D. Base: Close to 157D. Color, mature: Apex: Close to 154D. Mid-section: Close to 145C. Base: Close to 157D.

*Phyllaries.*—Number of phyllaries per inflorescence: About 50 arranged in about four whorls. Length: About 6 mm to 8 mm. Width: About 1.5 mm. Shape: Narrowly lanceolate. Apex: Acute. Base: Truncate. Margin: Entire. Texture, upper and lower surfaces: Smooth, glabrous. Color, upper surface: Close to 137A. Color, lower surface: Close to 137C.

*Peduncles.*—Length: About 1.4 cm. Diameter: About 2 mm. Angle: Upright. Strength: Strong, flexible. Texture: Sparsely pubescent. Color: Close to 137C.

*Reproductive organs.*—Androecium: Present on disc florets only. Filament length: About 1 mm. Filament color: Close to 157D. Anther shape: Narrowly elongated. Anther length: About 1.5 mm. Anther color: Close to 2B. Pollen amount: None observed. Gynoecium: Present on both ray and disc florets. Pistil length: About 7 mm. Stigma shape: Bi-parted. Stigma color: Close to 4B. Style length: About 4 mm. Style color: Close to 157D. Ovary color: Close to 155A.

*Seed/fruit.*—Seed and fruit production have not been observed.

Disease/pest resistance: Tolerance to Powdery Mildew has been observed on plants of the new *Aster*. Resistance to pests and other pathogens common to *Asters* has not been observed on plants grown under commercial conditions.

Garden performance: Plants of the new *Aster* have been observed to be rain and wind tolerant and to tolerate temperatures from about 2° C. to about 35° C.

It is claimed:

1. A new and distinct *Aster* plant named 'Kiastgrana' as illustrated and described.

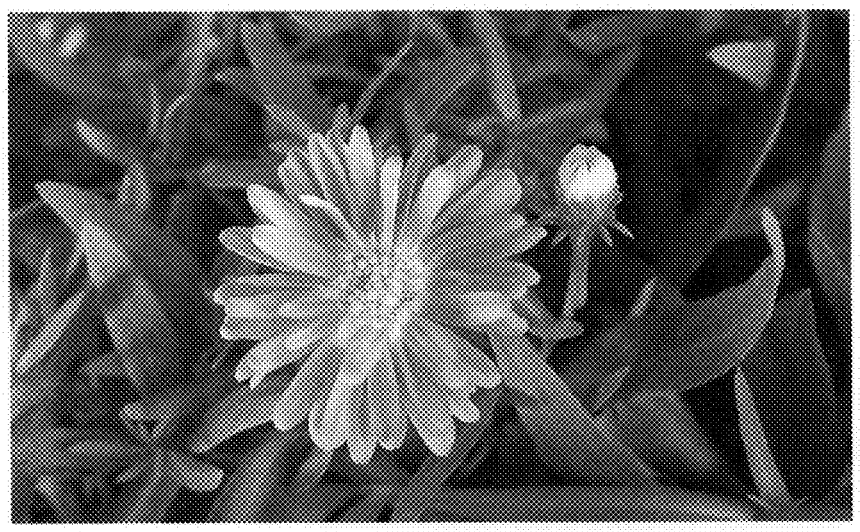
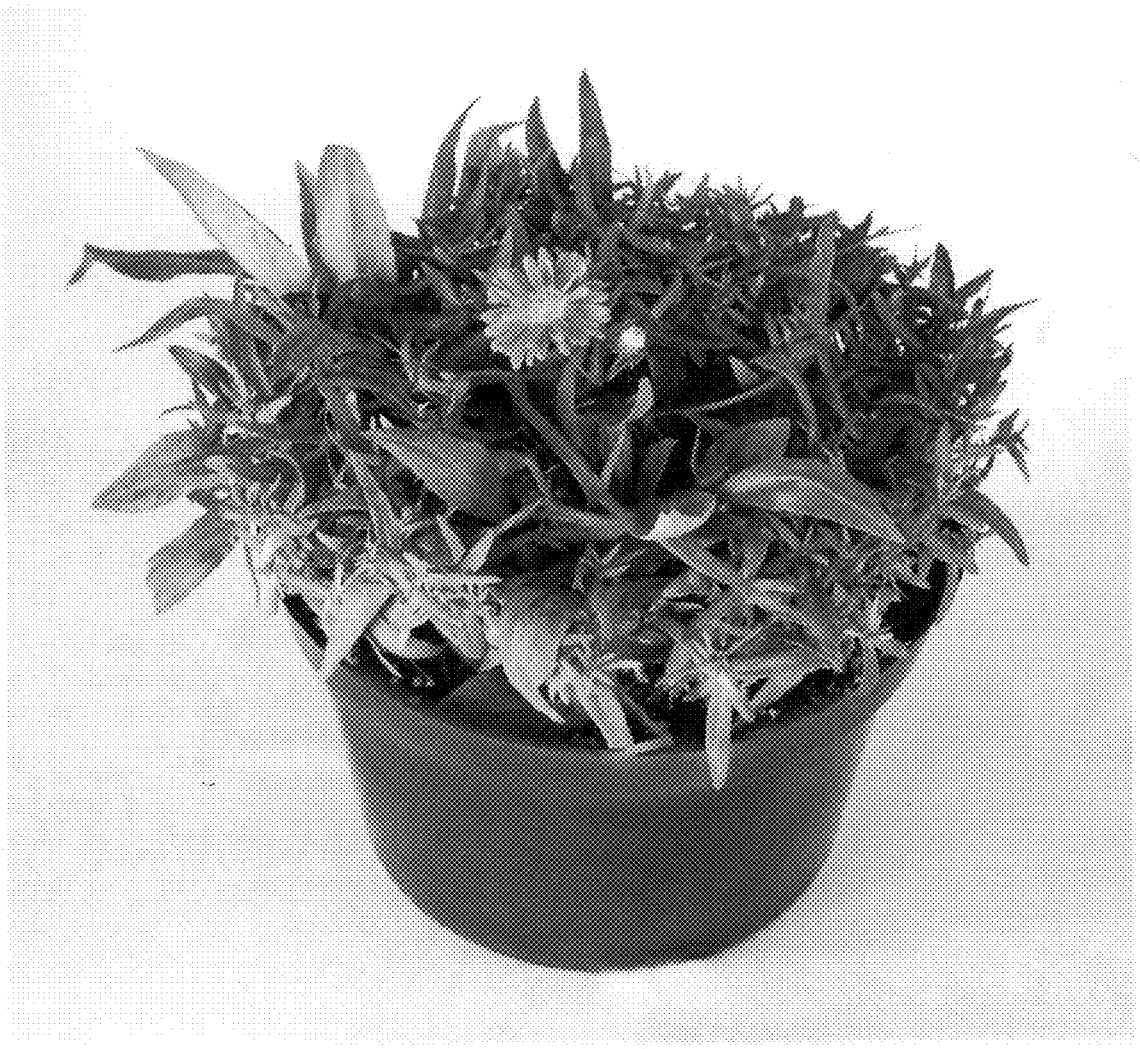

* * * * *